US010369316B2

(12) United States Patent
McCaslin et al.

(10) Patent No.: US 10,369,316 B2
(45) Date of Patent: Aug. 6, 2019

(54) FORHEAD GAS SUPPLY ASSEMBLY FOR A PATIENT INTERFACE SYSTEM

(75) Inventors: Jonathan Paul McCaslin, Renfrew, PA (US); Derrick Blake Andrews, Markleton, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 774 days.

(21) Appl. No.: 14/348,624

(22) PCT Filed: Sep. 14, 2012

(86) PCT No.: PCT/IB2012/054810
§ 371 (c)(1),
(2), (4) Date: Mar. 31, 2014

(87) PCT Pub. No.: WO2013/050893
PCT Pub. Date: Apr. 11, 2013

(65) Prior Publication Data
US 2014/0224255 A1    Aug. 14, 2014

Related U.S. Application Data

(60) Provisional application No. 61/542,839, filed on Oct. 4, 2011.

(51) Int. Cl.
*A61M 16/06*    (2006.01)
*A61M 16/00*    (2006.01)
*A61M 16/08*    (2006.01)

(52) U.S. Cl.
CPC .... *A61M 16/0633* (2014.02); *A61M 16/0057* (2013.01); *A61M 16/06* (2013.01);
(Continued)

(58) Field of Classification Search
CPC .............. A61M 16/06; A61M 16/0605; A61M 16/0611; A61M 16/0616; A61M 16/0622;
(Continued)

(56) References Cited

U.S. PATENT DOCUMENTS 5,538,000 A * 7/1996 Rudolph ............... A61M 16/06
128/201.22
6,427,694 B1   8/2002 Hecker
(Continued)

FOREIGN PATENT DOCUMENTS

| DE | 10331837 B3 | 1/2005 |
| WO | WO2011022779 A1 | 3/2011 |
| WO | WO2011110962 A1 | 9/2011 |

*Primary Examiner* — Jan Christopher L Merene
*Assistant Examiner* — Joseph D. Boecker
(74) *Attorney, Agent, or Firm* — Michael W. Haas

(57) ABSTRACT

A patient interface system includes a patient interface device, a conduit coupled to the patient interface device, and a gas supply assembly. The gas supply assembly includes a body portion having a first end, a second end disposed opposite and distal from the first end, a lower segment, and an upper segment attached to the lower segment. The first end includes a first coupling portion coupled to the patient interface device. The second end includes a second coupling portion coupled to the conduit. The upper segment and the lower segment together form an air channel extending between the first coupling portion and the second coupling portion. The first end is configured to be substantially disposed on the patient's forehead. The second end is configured to position the conduit away from the patient's face.

18 Claims, 3 Drawing Sheets

(52) U.S. Cl.
CPC .... *A61M 16/0638* (2014.02); *A61M 16/0683* (2013.01); *A61M 16/08* (2013.01); *A61M 16/0833* (2014.02); *A61M 16/0875* (2013.01); *A61M 16/0816* (2013.01)

(58) Field of Classification Search
CPC .......... A61M 16/0633; A61M 16/0638; A61M 16/0655; A61M 16/0683; A61M 16/08; A61M 16/0816; A61M 16/0833; A61M 16/0875
See application file for complete search history.

(56) References Cited

U.S. PATENT DOCUMENTS

| | | | |
|---|---|---|---|
| 6,494,207 B1 * | 12/2002 | Kwok | A61M 16/06 128/206.27 |
| 7,089,941 B2 * | 8/2006 | Bordewick | A61M 16/0666 128/206.21 |
| 7,845,353 B2 | 12/2010 | Bordewick | |
| 7,931,023 B2 * | 4/2011 | Berthon-Jones | A61M 16/00 128/204.18 |
| 2003/0075180 A1 | 4/2003 | Raje | |
| 2006/0081250 A1 | 4/2006 | Bordewick | |
| 2006/0213521 A1 | 9/2006 | Radney | |
| 2006/0283452 A1 * | 12/2006 | Woodard | A61M 16/06 128/205.25 |
| 2006/0283456 A1 | 12/2006 | Geiselhart | |
| 2006/0283460 A1 | 12/2006 | Brown | |
| 2007/0240721 A1 | 10/2007 | Ho | |
| 2007/0289597 A1 * | 12/2007 | Masella | A61M 25/02 128/207.18 |
| 2008/0047560 A1 | 2/2008 | Veliss | |
| 2008/0168991 A1 * | 7/2008 | Eifler | A61M 16/06 128/205.25 |
| 2008/0196727 A1 * | 8/2008 | Ho | A61M 16/06 128/207.11 |
| 2009/0143740 A1 * | 6/2009 | Bierman | A61M 5/1415 604/177 |
| 2012/0174922 A1 * | 7/2012 | Virr | A61M 16/0066 128/203.12 |
| 2013/0152918 A1 * | 6/2013 | Rummery | A61M 16/00 128/201.22 |

* cited by examiner

FORHEAD GAS SUPPLY ASSEMBLY FOR A PATIENT INTERFACE SYSTEM

CROSS-REFERENCE TO RELATED APPLICATIONS

This patent application claims the priority benefit under 35 U.S.C. § 371 of international patent application no. PCT/IB2012/054810, filed Sep. 14, 2012, which claims the priority benefit under 35 U.S.C. § 119(e) of U.S. Provisional Application No. 61/542,839 filed on Oct. 4, 2011, the contents of which are herein incorporated by reference.

BACKGROUND OF THE INVENTION

1. Field of the Invention

The present invention relates to a patient interface system, and, in particular, to a patient interface system including a forehead gas supply assembly.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device including a mask component on the face of a patient. The mask component may be, without limitation, a nasal mask that covers the patient's nose, a nasal cushion that rests beneath the patient's nose (such as a "pillows" style nasal cushion having nasal prongs that are received within the patient's nares or a "cradle" style nasal cushion that rests beneath and covers the patient's nares), a nasal/oral mask that covers the nose and mouth, or a full face mask that covers the patient's face. The patient interface device interfaces the ventilator or pressure support device with the airway of the patient through tubing, so that a flow of breathing gas can be delivered from the pressure/flow generating device to the airway of the patient. It is known to maintain such devices on the face of a wearer by a headgear having one or more straps adapted to fit over/around the patient's head.

For such patient interface devices, a key engineering challenge is to balance patient comfort against mask stability. This is particularly true in the case of treatment of OSA, where such patient interface devices are typically worn for an extended period of time. Many patients complain about the torque that the conduit or tubing used to supply the flow of breathing gas applies to their mask while they are sleeping. As a patient changes sleeping positions through the course of the night, such torque can cause issues such as discomfort and/or air leaks due to the mask becoming dislodged. Some patients, therefore, try to reroute the tubing above their head for better mask stability. However, the tubing is bulky and no mechanism or method is provided to secure the tubing to the top of the head.

Known patient interface devices that attempt to route the tubing above the patient's head include numerous components that must be assembled, and which increase overall cost. The numerous components also cause the mask to be large and bulky, which is undesirable for appearance, stability on the patient's head, and overall comfort.

SUMMARY OF THE INVENTION

Accordingly, it is an object of the present invention to provide a patient interface device that overcomes the shortcomings of conventional patient interface devices. This object is achieved according to one embodiment of the invention by providing a patient interface system including a forehead gas supply assembly.

It is yet another object of the present invention to provide a method of delivering a flow of breathing gas that does not suffer from the disadvantages associated with conventional techniques. This object is achieved by providing a method that includes positioning the conduit, which supplies the flow of breathing gas, proximate the top of the patient's head, away from the patient's face.

In one embodiment, a gas supply assembly is provided for a patient interface system. The gas supply assembly includes a body portion having a first end, a second end disposed opposite and distal from the first end, a lower segment, and an upper segment attached to the lower segment. The first end includes a first coupling portion coupled to a patient interface device. The second end includes a second coupling portion coupled to a conduit. The upper segment and the lower segment together form an air channel extending between the first coupling portion and the second coupling portion. The first end is configured to be substantially disposed on the patient's forehead. The second end is configured to position the conduit away from the patient's face.

In another embodiment, a method of delivering a flow of breathing gas to a patient is provided that includes providing a gas supply assembly having a body portion with a first end, a second end disposed opposite and distal from the first end, a lower segment, and an upper segment attached to the lower segment. The first end includes a first coupling portion coupled to a patient interface device. The second end includes a second coupling portion coupled to a conduit. The upper segment and the lower segment together form an air channel extending between the first coupling portion and the second coupling portion. The method further includes securing the gas supply assembly on the patient's forehead, positioning the conduit away from the patient's face, and delivering the flow of breathing gas through the gas supply assembly to the patient interface device.

These and other objects, features, and characteristics of the invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
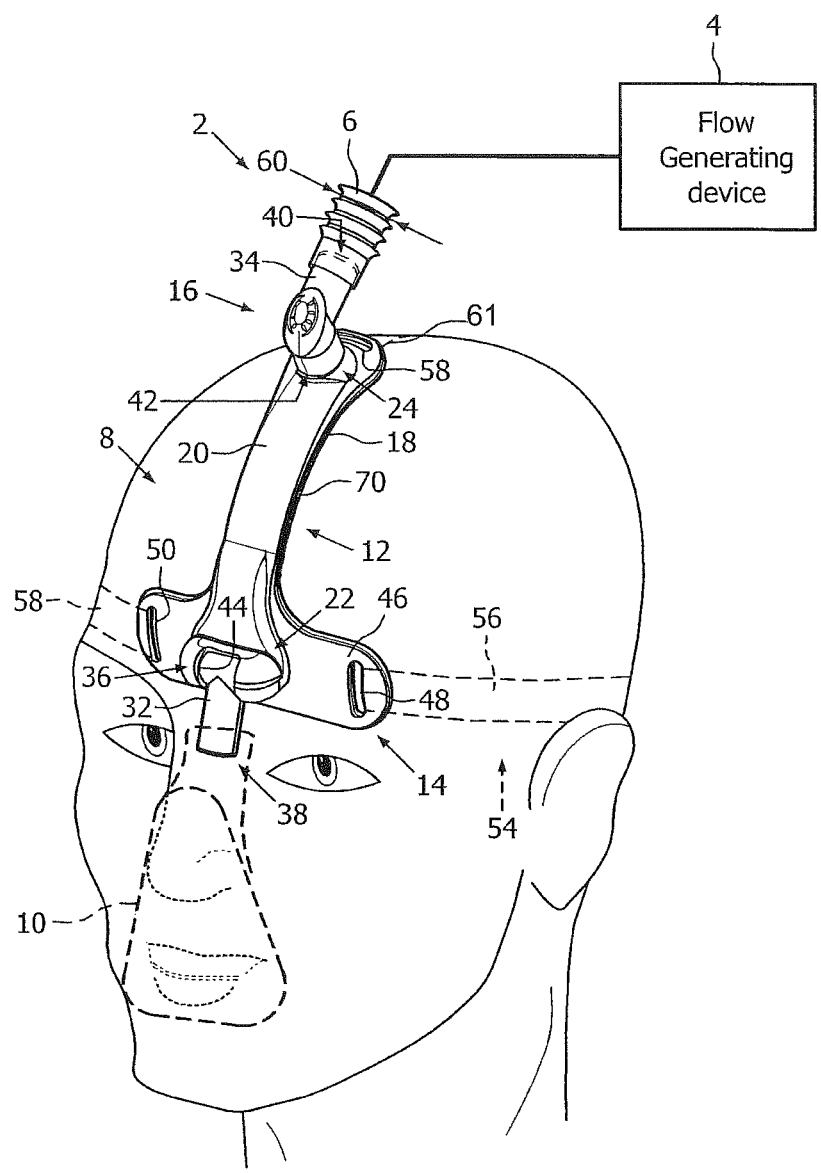
FIG. 1 is a simplified view of a system adapted to provide a regimen of respiratory therapy to a patient according to one exemplary embodiment of the invention.
Figure 2:
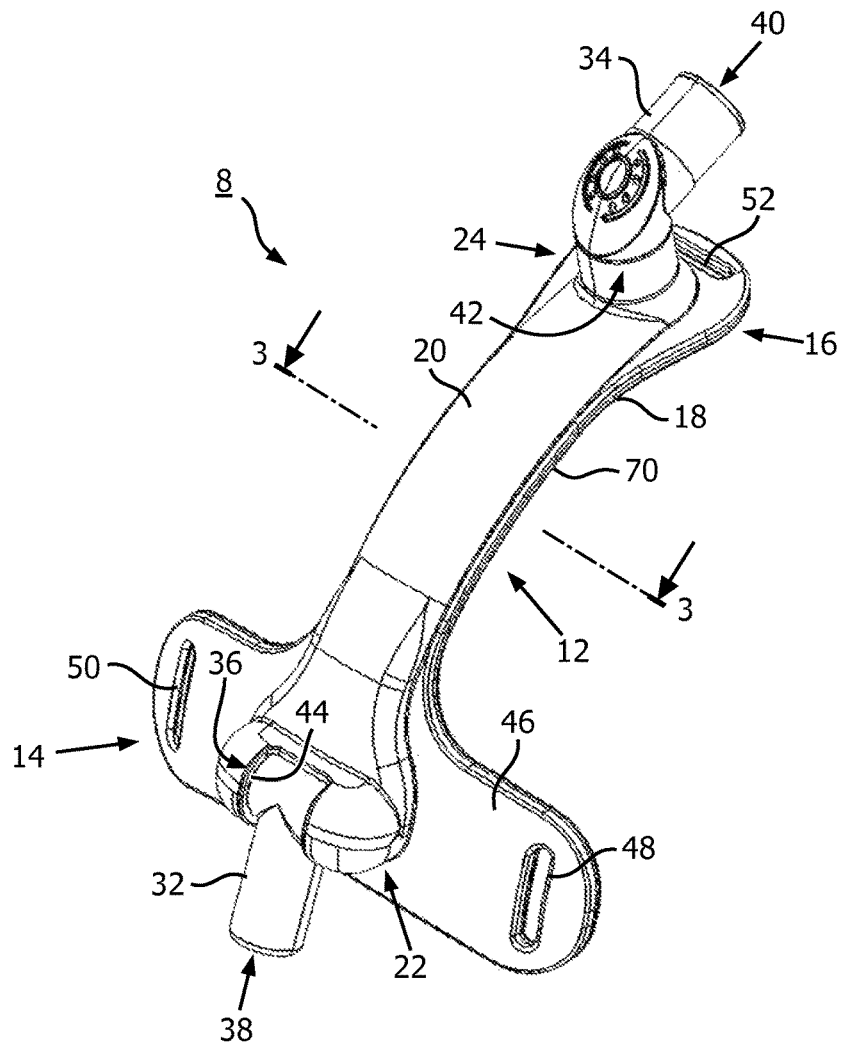
FIG. 2 is a front isometric view of a forehead gas supply assembly forming a part of the patient interface system of FIG. 1.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "attached" and "directly coupled" mean that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

A system 2 adapted to provide a regimen of respiratory therapy to a patient according to one exemplary embodiment is generally shown in FIG. 1. System 2 includes a flow generating device 4, a delivery conduit 6 (see, for example, tubing 6, partially shown in FIG. 1), a gas supply assembly 8, and a patient interface device 10. Flow generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Conduit 6 is structured to communicate the flow of breathing gas from flow generating device 4 to patient interface device 10 through conduit 6 and gas supply assembly 8. Conduit 6 and patient interface device 10 are often collectively referred to as a patient circuit.

In FIG. 1, patient interface device 10 is a nasaVoral mask. However, other types of patient interface devices, such as, for example and without limitation, a full face mask, which facilitates the delivery of the flow of breathing gas to the airway of a patient, may be alternatively employed, without departing from the scope of the present invention.

Gas supply assembly 8 includes a body portion 12 having first and second opposing ends 14,16, a lower segment 18, and an upper segment 20. Upper segment 20 is attached to lower segment 18, as best shown in the cross section view of FIG. 3. It will be appreciated that sections 18,20 can be attached using any known or suitable means such as, for example and without limitation, welding. First end 14 includes a first coupling portion 22 structured to be coupled to patient interface device 10. Second end 16 includes a second coupling portion 24 structured to be coupled to conduit 6 (partially shown in FIG. 1).

Figure 3:
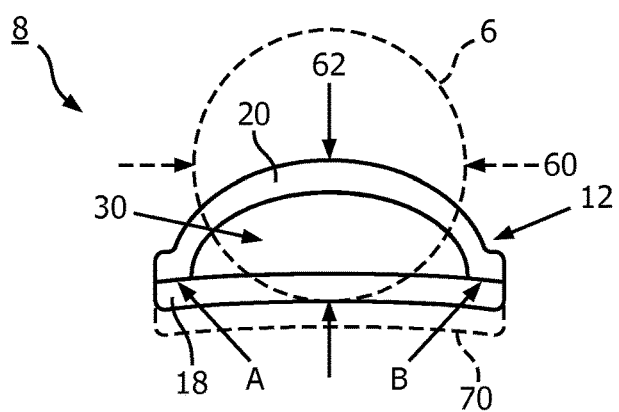
FIG. 3 is a section view taken along line 3-3 of FIG. 2.

As best shown in FIG. 3 upper segment 20 and lower segment 18 together form an air channel 30, which extends between first coupling portion 22 and second coupling portion 24. First end 14 is configured to be substantially disposed on the patient's forehead, and second end 16 is configured to position conduit 6 away from the patient's face, as shown in FIG. 1. Accordingly, among other advantages, forehead gas supply assembly 8 substantially eliminates disadvantages associated with known patient interface devices such as, for example, and without limitation, torque, leaks, discomfort, bulky size, and other issues associated with conduit being disposed around the patient's face.

Figure 4:
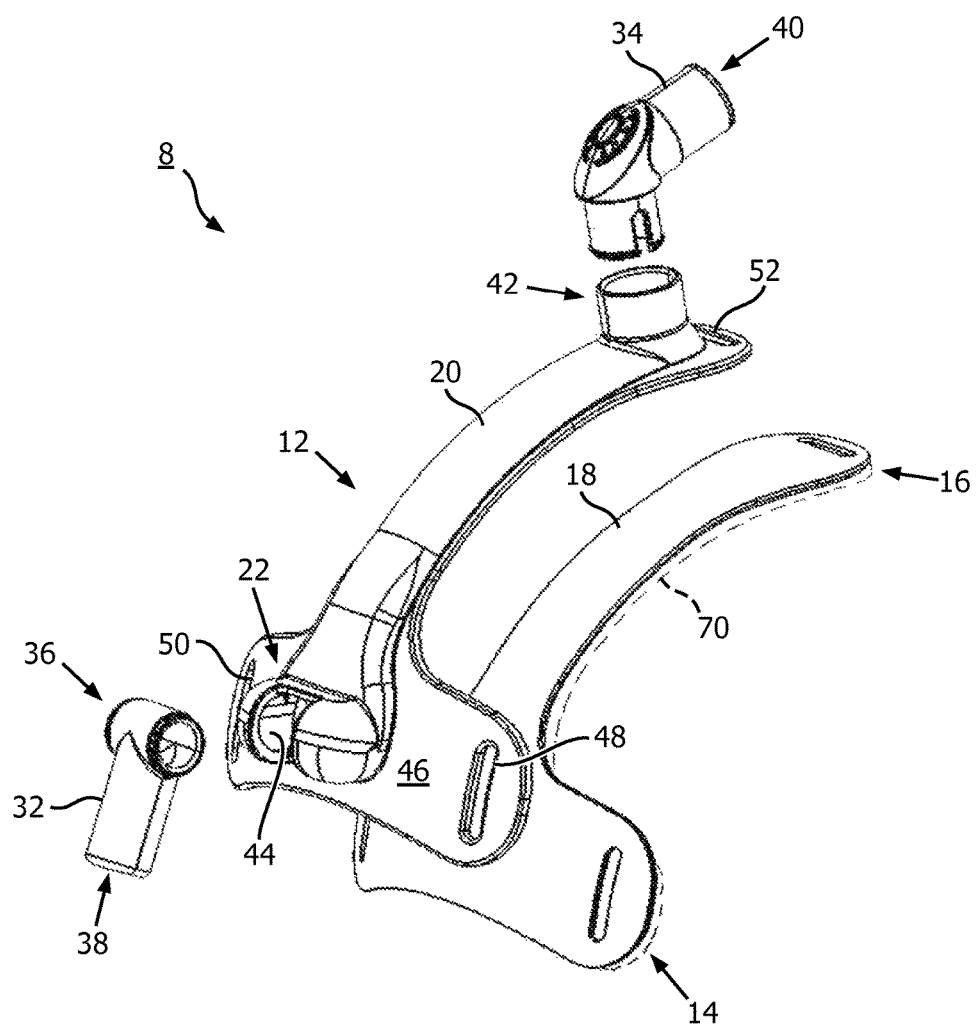
FIG. 4 is an exploded isometric view of the forehead gas supply assembly forming part of the patient interface system of FIG. 1.

Preferably, although not required, gas supply assembly 8 further includes a first fluid coupling device 32 and a second fluid coupling device 34. An inlet end 36 of first fluid coupling device 32 is coupled to first coupling portion 36, and an outlet end 38 of first fluid coupling device 32 is coupled to patient interface 10 (see, for example and without limitation, FIG. 1). Inlet end 40 of second fluid coupling device 34 is coupled to conduit 6 and outlet end 42 of second fluid coupling device 34 is coupled to second coupling portion 24. In the exemplary embodiment, first coupling portion 22 includes a socket 44, which is formed in a first end 14 of body portion 12, as best shown in the exploded view of FIG. 4.

In the non-limiting example shown and described herein, first fluid coupling member is a T-fitting 32, wherein inlet end 36 of T-fitting 32 is pivotably disposed in socket 44, and patient interface device 10 is a mask (shown in simplified form in phantom line drawing in FIG. 1). Outlet end 38 of T-fitting 32 is attached to mask 10. It will be appreciated, however, that T-fitting 32 or any known or suitable alternative fluid coupling device (not shown) could be directly, or indirectly, coupled to any known or suitable patient interface device, without departing from the scope of the invention. Similarly, the exemplary second fluid coupling device 34 is an elbow, although it will be appreciated that any known or suitable alternative fluid coupling device (not shown) could be employed, in accordance with the invention.

Gas supply assembly 8 further includes a laterally extending attachment portion 46 disposed at or about first end 14 of body portion 12. Laterally extending attachment portion 46 preferably includes a first aperture 48 and a second aperture 50. In the exemplary embodiment shown in FIG. 1, second end 16 of body portion 12 has a third aperture 52. First aperture 48, second aperture 50, and third aperture 52 are configured to cooperate with a suitable headgear assembly 54 (partially shown in simplified form in phantom line drawing in FIG. 1) to adjustably secure gas supply assembly 8 to the patient's head. More specifically, in the non-limiting example shown in FIG. 1, headgear assembly 54 includes strap 56 attached to laterally extending attachment portion 46 at aperture 48, strap 58 attached to laterally extending attachment portion 46 at aperture 50, and strap 61 attached to second end 16 of body portion 12 at aperture 52. Thus, headgear assembly 54 can be adjusted, as necessary, to secure gas supply assembly 8 to the forehead region of patient, in the desired manner. It will, therefore, be appreciated that conduit 6 is advantageously disposed proximate the top of patient's head, away from patient's face.

Referring to FIG. 3, a simplified rendition of conduit 6 has been drawn overlaying body portion 12 of gas supply assembly 8, solely for purposes of showing the advantageous low-profile nature of gas supply assembly 8. Specifically, it will be appreciated that conduit 6 has a diameter 60 (see also FIG. 1), and that body portion 12 has a thickness 62, which is defined by the combined depth of lower segment 18, upper segment 20, and air channel 30 disposed therebetween. Thickness 62 of body portion 12 is substantially less than diameter 60 of conduit 6, as shown. For example and without limitation, in one non-limiting embodiment, thickness 62 (e.g., the distance or height that body portion 12 of gas supply assembly 8 extends outwardly from patient's forehead) is less than half of diameter 60 of conduit 6. It will, therefore, be appreciated that gas supply assembly 8 provides a low-profile mechanism for supplying a flow of gas from a location proximate the top of patient's head using a well-positioned conduit 6 arrangement, and advantageously reduces the overall bulk of patient interface system 2.

Gas supply assembly 8 optionally further includes a pad 70, or other known or suitable comfort mechanism, configured to be disposed between lower segment 18 of body portion 12 and the patient's forehead. For example and without limitation, pad 70 is shown in FIGS. 1-4 being glued or otherwise suitably secured to lower segment 18. In the non-limiting example, shown, pad 70 has substantially the same shape as lower segment 18. Accordingly, pad 70 enhances patient comfort when gas supply assembly 8 is secured to patient's forehead.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A gas supply assembly for a patient interface system, the patient interface system including a patient interface device and a conduit for delivering a flow of breathing gas from a flow generating device to an airway of a patient, the gas supply assembly comprising:
   a body portion having a first end, a second end disposed opposite and distal from the first end, a lower segment, and an upper segment attached to the lower segment, the first end including a first coupling portion structured to be coupled to the patient interface device, the second end including a second coupling portion structured to be coupled to the conduit, wherein the upper segment and the lower segment together form an air channel extending between the first coupling portion and the second coupling portion, wherein the first end is configured to be substantially disposed on the patient's forehead, and wherein the second end is configured to position the conduit away from the patient's face; and
   a fluid coupling device having an inlet end and an outlet end, wherein the inlet end of the fluid coupling device is coupled to the first coupling portion and the outlet end of the fluid coupling device is coupled to the patient interface device, wherein the first coupling portion includes a socket formed in the first end of the body portion, wherein the fluid coupling device is a T-fitting, and wherein the inlet end of the T-fitting is pivotably disposed in the socket, wherein the conduit has a diameter, and wherein the body portion including the air channel formed therein has a thickness which is substantially less than the diameter of the conduit such that the gas supply assembly has a low-profile relative to the patient's face.

2. The gas supply assembly of claim 1, further comprising a second fluid coupling device having an inlet end and an outlet end, and wherein the inlet end of the second fluid coupling device is coupled to the conduit and the outlet end of the second fluid coupling device is coupled to the second coupling portion.

3. The gas supply assembly of claim 1, wherein the thickness of the body portion is defined by a combined depth of the lower segment, the upper segment, and the air channel therebetween, and wherein the thickness of the body portion is less than half of the diameter of the conduit.

4. The gas supply assembly of claim 1, further comprising a pad configured to be disposed between the lower segment of the body portion and the patient's forehead.

5. The gas supply assembly of claim 1, wherein the lower segment has a perimeter portion, and wherein the upper segment has a perimeter portion overlaying and being shaped the same as the perimeter portion of the lower segment.

6. The gas supply assembly of claim 1, wherein the patient interface device is a mask, and wherein the outlet end of the T-fitting is attached to the mask.

7. The gas supply assembly of claim 1, wherein the first end of the body portion further includes a laterally extending attachment portion having a first aperture and a second aperture, wherein the second end of the body portion has a third aperture, and wherein the first aperture, the second aperture, and the third aperture are configured to cooperate with a head gear assembly to adjustably secure the gas supply assembly to the patient's head.

8. A gas supply assembly for a patient interface system, the patient interface system including a patient interface device and a conduit for delivering a flow of breathing gas from a flow generating device to an airway of a patient, the gas supply assembly comprising:
   a body portion having a first end, a second end disposed opposite and distal from the first end, a lower segment, and an upper segment attached to the lower segment, the first end including a first coupling portion structured to be coupled to the patient interface device, the second end including a second coupling portion structured to be coupled to the conduit, wherein the upper segment and the lower segment together form an air channel extending between the first coupling portion and the second coupling portion, wherein the first end is configured to be substantially disposed on the patient's forehead, and wherein the second end is configured to position the conduit away from the patient's face, a fluid coupling device having an inlet end and an outlet end, wherein the inlet end of the fluid coupling device is coupled to the conduit and the outlet end of the fluid coupling device is coupled to the second coupling portion, wherein the conduit has a diameter, and wherein the body portion including the air channel formed therein has a thickness which is substantially less than the diameter of the conduit such that the gas supply assembly has a low-profile relative to the patient's face, and wherein the fluid coupling device is an elbow.

9. The gas supply assembly of claim 8, further comprising a T-fitting having an inlet end and an outlet end, wherein the first coupling portion includes a socket formed in the first end of the body portion, and wherein the inlet end of the T-fitting is pivotably disposed in the socket.

10. The gas supply assembly of claim 9, wherein the patient interface device is a mask, and wherein the outlet end of the T-fitting is attached to the mask.

11. The gas supply assembly of claim 8, wherein the lower segment has a perimeter portion, and wherein the upper segment has a perimeter portion overlaying and being shaped the same as the perimeter portion of the lower segment.

12. The gas supply assembly of claim 8, wherein the first end of the body portion further includes a laterally extending attachment portion having a first aperture and a second aperture, wherein the second end of the body portion has a third aperture, and wherein the first aperture, the second aperture, and the third aperture are configured to cooperate with a head gear assembly to adjustably secure the gas supply assembly to the patient's head.

13. The gas supply assembly of claim 8, wherein the thickness of the body portion is defined by a combined depth of the lower segment, the upper segment, and the air channel therebetween, and wherein the thickness of the body portion is less than half of the diameter of the conduit.

14. The gas supply assembly of claim 8, further comprising a pad configured to be disposed between the lower segment of the body portion and the patient's forehead.

15. A gas supply assembly for a patient interface system, the patient interface system including a patient interface device and a conduit for delivering a flow of breathing gas from a flow generating device to an airway of a patient, the gas supply assembly comprising:

a body portion having a first end, a second end disposed opposite and distal from the first end, a lower segment, and an upper segment attached to the lower segment, the first end including a first coupling portion structured to be coupled to the patient interface device, the second end including a second coupling portion structured to be coupled to the conduit, wherein the upper segment and the lower segment together form an air channel extending between the first coupling portion and the second coupling portion, wherein the first end is configured to be substantially disposed on the patient's forehead, and wherein the second end is configured to position the conduit away from the patient's face, wherein the conduit has a diameter, wherein the body portion including the air channel formed therein has a thickness which is substantially less than the diameter of the conduit such that the gas supply assembly has a low-profile relative to the patient's face, wherein the first end of the body portion further includes a laterally extending attachment portion having a first aperture and a second aperture, wherein the second end of the body portion has a third aperture, and wherein the first aperture, the second aperture, and the third aperture are configured to cooperate with a head gear assembly to adjustably secure the gas supply assembly to the patient's head.

16. The gas supply assembly of claim 15, wherein the lower segment has a perimeter portion, and wherein the upper segment has a perimeter portion overlaying and being shaped the same as the perimeter portion of the lower segment.

17. The gas supply assembly of claim 15, wherein the thickness of the body portion is defined by a combined depth of the lower segment, the upper segment, and the air channel therebetween, and wherein the thickness of the body portion is less than half of the diameter of the conduit.

18. The gas supply assembly of claim 15, further comprising a pad configured to be disposed between the lower segment of the body portion and the patient's forehead.

* * * * *